United States Patent [19]

Adams et al.

[11] 4,039,652
[45] Aug. 2, 1977

[54] COLUMN METHOD OF IMMUNOASSAY EMPLOYING AN IMMOBILIZED BINDING PARTNER

[75] Inventors: Ernest Clarence Adams; Joe William Davis; John Menley Yoder, all of Elkhart, Ind.

[73] Assignee: Miles Laboratories, Inc., Elkhart, Ind.

[21] Appl. No.: 405,316

[22] Filed: Oct. 11, 1973

[51] Int. Cl.$^2$ .................... G01N 33/00; G01N 33/16; G21H 5/02
[52] U.S. Cl. ..................................... 424/1; 23/230 B; 23/230.6; 424/12; 250/303; 424/1.5
[58] Field of Search ............................. 424/1.5, 1, 12; 23/230 B, 230.6; 250/303

[56] References Cited

U.S. PATENT DOCUMENTS

| | | | |
|---|---|---|---|
| 3,284,434 | 11/1966 | Sutherland | 424/12 X |
| 3,555,143 | 6/1967 | Axen et al. | 424/1 |
| 3,592,888 | 7/1971 | Wolf | 424/1 |
| 3,652,761 | 3/1972 | Weetall | 424/12 |
| 3,720,760 | 3/1973 | Bennich et al. | 424/1 |
| 3,791,932 | 2/1974 | Schuurs et al. | 23/230 B X |
| 3,843,444 | 10/1974 | Likhite | 424/12 X |
| 3,961,894 | 6/1976 | Gordon et al. | 23/230.6 |

OTHER PUBLICATIONS

Miles et al., Nature, vol. 219, July 13, 1968, pp. 186–189.
Goodfriend et al, Immunochemistry, vol. 6, May 1969, pp. 481–484.
Catt et al., Biochem. J., vol. 100, 1966, pp. 31c–33c.
Kirkham and Hunter, Ed., Radioimmunoassay Methods, 1970, pp. 405–412.

*Primary Examiner*—Benjamin R. Padgett
*Assistant Examiner*—Christine M. Nucker
*Attorney, Agent, or Firm*—Andrew L. Klawitter

[57] ABSTRACT

An improved method is disclosed for determining substances in a fluid sample having a mutual specific binding affinity, such as antigens and antibodies, said method utilizing a device comprising a column containing an insoluble porous matrix with which specific binding partners to the substance being determined are immobilized, preferably by chemically coupling them to the matrix material. The method comprises allowing a fluid sample containing the substance to be determined, a reference sample containing a labeled form of either the substance under determination or a specific binding partner, and an eluting liquid to flow through the device, followed by a determination of the relative amount of the labeled component retained in or eluted from the column. Comparison to standard values affords a reading of the concentration or absolute amount of the substance being determined in the fluid sample.

33 Claims, 1 Drawing Figure

U.S. Patent  Aug. 2, 1977  4,039,652
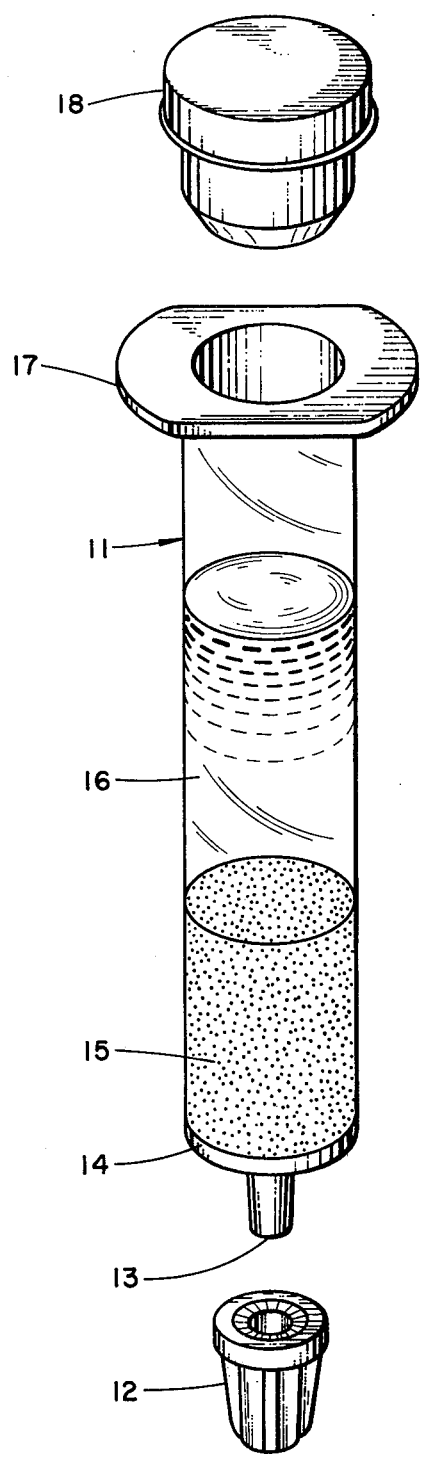

COLUMN METHOD OF IMMUNOASSAY EMPLOYING AN IMMOBILIZED BINDING PARTNER

BACKGROUND OF THE INVENTION

Specific binding substances are those substances which interact with specific binding partners to form a bond therebetween to the exclusion of other substances. The bond formed is generally a physical bond, but in some instances it may be termed a physiochemical bond or even a chemical bond. It may be said that a specific binding substance and its specific binding partner have an affinity to bind or react with one another. Specific binding substances are generally either peptides, proteins, carbohydrates, glycoproteins, or steroids. Some examples of specific binding pairs, which comprise a specific binding substance and its specific binding partner, are antigens and their antibodies, haptens and their antibodies, enzymes and their substrates, hormones and their receptors, and vitamins and their receptors.

As used herein, the term specific binding substance may refer either to the substance being determined or its specific binding partner; the term specific binding pair refers to a specific binding substance and a specific binding partner therefor; the term unknown or unknown substance refers to the substance being determined; and the term labeled component refers to a labeled form of either the substance being determined or a specific binding partner.

Assay methods for determining specific binding substances are based on the ability of such substances to react with their specific binding partners in labeled form in a manner similar to that in which they react in their unlabeled form. There are basically three approaches to the quantitative determination of specific binding substances using such an assay method. The equilibrium method is founded on the competition between the unknown and the labeled form of the substance being determined for a limited quantity of specific binding partners. The saturation method has its basis in the saturation of a portion of a quantity of binding partners with the unknown, followed by the reaction of the remaining unbound partners with a quantity of the labeled form of the substance being determined. The direct method is based on adding the unknown to a quantity of specific binding partners, followed by the addition of excess specific binding partners in a labeled form in order to bind with all of the bound unknown. All of these methods provide quantitative determinations through calculations based on the extent of binding of the labeled component. Specific binding assays may be termed immunoassays where antigens, haptens, or antibodies are involved, and may be termed radioimmunoassays where the same are involved and where the label is a radioactive label.

The introduction of the two-phase system, consisting of a fluid phase and a solid phase, to specific binding assays has greatly simplified these assays. In such two-phase systems, the solid phase consists of the binding partners in an insolubilized form. The utilization of techniques involving adsorption, chemical coupling, and physical entrapment provides means of insolubilizing the binding partners. The advantage of the two-phase system lies primarily in the ease of separation of bound labeled component from unbound labeled component.

Specific binding assays find utility in a vast number of areas. The fields of research, medicine and industry all find use in such an advantageous technique. These methods may be applied to the wide range of substances possessing a specific binding affinity for a binding partner and provide determinations which are specific, sensitive, precise and reliable compared to alternative methods.

DESCRIPTION OF THE PRIOR ART

The separation of the labeled component which is bound to its binding partner from that which is unbound is critical to specific binding assays. In general, the rate and reliability with which this separation is accomplished bears directly upon the rate and reliability of the assay as a whole. Various methods based on a two-phase system employing insolubilized binding partners have been developed aimed at quick, reliable determinations. The techniques employed in insolubilizing the binding partners in conjunction with specific binding assays include pre-precipitation of the binding partner, sometimes referred to as a double antibody method where the binding partner is an antibody, entrapment of the binding partner within an acrylamide gel, and polymerization of the binding partner. The techniques of chemically binding or coupling the binding partner to an insoluble polymer or absorbing it to the inner surface of an assay test tube are more commonly used. A vast number of known procedures for coupling binding partners to a variety of polymers are available for use in conjunction with a two-phase specific binding assay system.

At the present time, the known specific binding assays which utilize insolubilized binding partners employ a closed or non-flow through system such as test tubes containing the insolubilized binding partners in a loose particle form, test tubes having the binding partners adsorbed to their inner surfaces, or syringes containing the binding partners in a gel entrapped form. Since samples of unknown are generally highly dilute and since the use of a closed system limits sample size, incubation times must be long in order to obtain reliable results. Recommended incubation times range from between 6 hours to 2 days with some much longer. Separation of the bound and unbound labeled component, even through the use of insolubilized binding partners, still requires excessive manipulation of the system such as centrifuging and extensive washing.

Flow-through systems utilizing insolubilized binding partners are limited in the prior art to techniques such as purification and concentration of dilute unknowns. In relation to specific binding assays, such systems have served only as preparatory steps to the actual assay in the prior art. Conventional specific binding assays are then performed on the purified, concentrated unknown, which assays remain time consuming and require much system manipulation.

In the context of this disclosure, determination of a substance in a fluid sample implies either the determination of the concentration or the absolute amount of that substance in the fluid sample.

SUMMARY OF THE INVENTION

It has now been found that by utilizing a two-phase, flow-through assay system in conjunction with either an equilibrium, a direct, or a saturation assay technique, a highly advantageous, rapid and reliable method and device is provided for quantitatively determining one of the substances comprising a specific binding pair of substances having a mutual specific binding affinity. Substances which may be determined include antigens and their antibodies, haptens and their antibodies, enzymes and their substrates, hormones and their receptors, and vitamins and their receptors. The disclosed test device basically comprises a column containing a matrix which is porous and insoluble with respect to the fluid containing the substance to be determined and which has a specific binding partner to said substance to be determined immobilized therewith.

The matrix preferably is made of a material comprising a polymeric substance. A specific binding partner to the substance to be determined is immobilized with the matrix preferably by being chemically bound to the matrix, in which case the matrix is preferably a polymer substance which contains a hydroxyl, primary amino, or secondary amino group. The immobilized specific binding partner is chemically bound to the matrix preferably through a coupling agent, preferably a cyanogen halide, an inorganic or organic cyanate, or an epihalohydrin.

The disclosed method basically comprises the steps of (a) bringing a predetermined quantity of a fluid sample containing the substance to be determined and a predetermined quantity of a reference sample containing a labeled component, which is a labeled form of one of the substances comprising a specific binding pair to which the substance to be determined belongs into contact with the matrix of the disclosed device; (b) bringing the matrix into contact with an eluting liquid capable of eluting from the column substantially all of the unbound labeled component originating from the reference sample and remaining after step (a), and (c) determining the relative amount of the labeled component which is retained in the column, which relative amount is a function of the amount of the substance to be determined in the fluid sample.

Following a saturation assay technique, the labeled component is a labeled form of the substance being determined and step (a) is accomplished by (a) (1) contacting the matrix with a predetermined quantity of the fluid sample so that some of specific binding partners immobilized with the matrix remain unbound, and (a) (2) thereafter contacting the matrix with a predetermined quantity of the reference sample, the amount of specific binding partners immobilized with the matrix being in excess of that capable of binding with the total amount of the substance to be determined in said predetermined quantity of fluid sample contacted with said matrix in step (a) (1) in the time that the predetermined quantity of fluid sample and the matrix are in contact prior to step (a) (2), and the amount of labeled component in said predetermined quantities of reference sample contacted with said matrix in step (a) (2) being sufficient to bind a portion or all of the remaining unbound immobilized specific binding partners in the time that the predetermined quantity of reference sample and the matrix and in contact prior to step (b). Preferably, the times of contact between the matrix and the predetermined quantities of the fluid and reference samples are prolonged for predetermined incubation periods, which may be the same or different and which are preferably between 15 minutes and 12 hours. An additional step may be included between the contacts of the matrix with the predetermined quantities of the fluid and reference sample which step is contacting the matrix with an eluting liquid, preferably comprising a buffer, capable of eluting from the column substantially all of the substance being determined which has not become bound.

Following an equilibrium assay technique, the labeled component is a labeled form of the substance being determined and step (a) is accomplished by either contacting the matrix with a mixture comprising predetermined quantities of the fluid and reference samples, the amount of specific binding partners immobilized with the matrix being in excess of that capable of binding with the total amount of both the substance to be determined in the fluid sample and the labeled component in the reference sample in the time that the mixture and the matrix are in contact prior to step (b); or by (a) (1) contacting the matrix with a predetermined quantity of the reference sample, and (a) (2) thereafter contacting the matrix with a predetermined quantity of the fluid sample, the amount of labeled component in the predetermined quantity of reference sample contacted with said matrix in step (a) (1) being in excess of that capable of binding with the amount of the specific binding partners immobilized with the matrix in the time that the predetermined quantity of reference sample and the matrix are in contact prior to step (a) (2), and the amount of the substance being determined in said predetermined quantity of fluid sample contacted with said matrix in step (a) (2) being sufficient to displace only a portion of the labeled component bound to the specific binding partners immobilized with the matrix in the time that the predetermined quantity of fluid sample and the matrix prior to step (b). Therefore, the amount of the labeled component which becomes bound to the matrix in step (a) (1) must be in excess of that capable of being completely displaced by the substance to be determined in the predetermined quantity of the fluid sample added in step (a) (2) in the time that the predetermined quantity of the fluid sample and the matrix are in contact prior to step (b). In both cases, the times of contact between the matrix and the predetermined quantities of the fluid and reference samples are preferably prolonged for predetermined incubation periods, which may be the same or different and which are preferably between 15 minutes and 12 hours.

Following a direct assay technique, the labeled component is a labeled form of a specific binding partner to said substance being determined and step (a) is accomplished by (a) (1) contacting the matrix with a predetermined quantity of the fluid sample, and (a) (2) thereafter contacting the matrix with a predetermined quantity of the reference sample, the amount of specific binding partners immobilized with the matrix being in excess of that capable of binding with the total amount of the substance to be determined in said predetermined quantity of fluid sample contacted with said matrix in step (a) (1) in the time that the predetermined quantity of fluid sample and the matrix are in contact prior to step (a) (2), and the amount of labeled component in the predetermined quantity of reference sample contacted with said matrix in step (a) (2) being sufficient to bind a portion or all of the substance being determined which is bound to the immobilized specific binding partners in the time that the predetermined quantity of reference sample and the matrix are in contact prior to step (b).

The eluting liquid used in step (b) preferably comprises a buffer. The additional step of equilibrating the column, preferably with a liquid comprising a buffer, prior to step (a) is also preferably included in the present method. The labeled component in the reference sample is preferably either radioactively labeled or labeled through the coupling of either an enzyme or its substrate to the component. Where the labeled component in the reference sample is radioactively labeled, step (c) is preferably accomplished by measuring the amount of radioactivity either emanating from the column or the amount of radioactivity present in the eluate from step (b), which amounts are a function of the amount of the unknown in the fluid sample. Where the labeled component in the reference sample is labeled through the coupling to either an enzyme or its substrate, step (c) is preferably accomplished by performing an appropriate enzymatic assay on the eluate from step (b) or on the washed column itself.

The relative amount of the labeled component found to have been retained in the column, by becoming specifically bound to immobilized binding partners, is preferably compared to standard values which are the relative amounts of labeled component found to be retained in the same or a similar column following the same procedure in assaying standard fluids containing various levels of known standard amounts of the substance to be determined.

DESCRIPTION OF THE DRAWING

The sole FIGURE in the drawing is an exploded perspective view of one form of the device disclosed herein.

DESCRIPTION OF THE PREFERRED EMBODIMENTS

The present invention's use of a two-phase specific binding assay method requires a solid phase which comprises insolubilized binding partners. By immobilizing the binding partners with a matrix which is insoluble, the binding partners are rendered insolubilized. The matrix may comprise any substance which is insoluble and porous with respect to the fluid phases, which possesses flow characteristics for effective contact with the fluid phases, and which is capable of immobilizing the specific binding partners. Such substances include various polymers, gels, colloids, fibrous webs, and so forth. The porosity should be such that there is substantial interaction between the fluid phases and the binding partners in a minimum amount of time so that the unknown and the labeled component come into quick and effective contact with the specific binding sites of the binding partners.

There exists a variety of methods for immobilizing the binding partners with an insoluble matrix. Such means include physical entrapment of the binding partners. Also, they may be polymerized or coupled to a substance to form a conjugate first, and then physically entrapped as a polymer or conjugate with the matrix. Such substances which form conjugates with the binding partners include latex, metacrylate and bacteria. Another means of immobilizing the binding partners is adsorption with a matrix. Such adsorption must be strong enough to effectively render the binding partners insoluble with respect to the flow of the fluid sample. Instances of matrices which lend themselves to immobilizing the binding partners through physical entrapment of either the binding partners themselves, a polymer of the binding partners, or a conjugate of the binding partners, include various complex polymers, colloids, and gels, such as acrylamide gel. Those which immobilize binding partners through adsorption include charcoal, glass and various plastics.

In the immobilization of the specific binding partners with the matrix, the specific binding sites of the binding partners should be kept as free of inhibition as possible with respect to their specific binding capacity for the unknown and the labeled components. Variations in pH, temperature, and other environmental conditions may affect the extent of such inhibition so that optimal conditions should be chosen. All reactions involving protein structures, such as is found in antigens, haptens, enzymes, hormones, receptors, and antibodies, should be accomplished at as low a temperature and as near normal a pH as possible to avoid irreversible denaturation and aggregation. Optimal conditions vary with the particular binding partner involved due to the structural variety found in such substances.

A preferred means of immobilizing the binding partners with the matrix is by chemically binding or coupling them to the matrix. The chemical bonding or coupling of the binding partners to the matrix insures their immobilization and provides one with a multitude of available techniques from which to choose. For a given binding partner the large number of chemically reactive groups present therein provide ready means of chemically bonding or coupling them to an appropriately chosen matrix.

Substances which lend themselves to immobilizing the binding partners through the formation of chemical bonds or couples, as is preferred, include various polymers, gels, colloids and fibrous webs. The binding partners may be either chemically bound to the matrix material directly or through a chemical coupling agent. Matrix materials which have been reacted with a coupling agent may be described as being activated to reactivity with respect to the chemically reactive sites of the binding partners. The fundamental chemically reactive sites in binding partners are free carboxyl groups, free amino groups, phenol groups, imidazole groups, imino groups, free thiol groups, guanidino structures, aliphatic hydroxyl groups, methyl mercapto groups, phenyl groups, amide groups, disulphide links, and peptide links. Substances capable of being activated to coupling reactivity include fibrous materials, such as cellulose derivatives; naturally occurring polymers, such as certain polysaccharides; and synthetic polymers.

The group of synthetic polymers provides a wide assortment of substances available for use in the composition of the matrix. Particularly preferred polymeric substances are those containing at least one chemical group which is either a hydroxyl, a primary amino, or a secondary amino group. Preferred coupling agents used in combination with the above are the cyanogen halides, such as cyanogen bromide; the inorganic and organic cyanates, such as the alkali metal cyanates; and the epihalohydrins, such as epichlorohydrin. Agarose activated with cyanogen bromide is particularly useful. Other coupling agents which may be used include diazo and hydrazine compounds, such as for use in activating polystyrenes, acrylamides, and derivatives thereof; glutaraldehyde, such as for use in activating partially hydrolized nylon; and so forth. The polymers which may be utilized may be in a dispersed form, a structurally integrated form, or any gradient in between. Such forms include powders, resins, membranes, and so forth.

The present invention discloses a device comprising a column which may basically be described as an elongated hollow body open at both ends. The column is preferably selectively sealable at one end. The column may be in any form which is capable of containing the solid phase and which provides means for introducing the liquid phases to the solid phase and for facilitating flow through the matrix. Such forms include linear and curved tubing, syringes, burettes, pipettes, and the like as well as conventional column apparatus. The column should be formed of a material which is inert with respect to the fluid phases in the sense that neither interfering material, the unknown nor the labeled component are able to be adsorbed or otherwise retained by the column material itself. Where the label is a radioactive label, the column preferably has a fixed geometry in order to provide a device which can be directly subjected to radioactivity measurements. The solid phase is contained within the column by such means as porous discs, bibulous plugs, permeable membranes, and the like, as well as by the internal molding configuration of the column itself. The containing means should be porous and inert with respect to the fluid phases so that such means do not retain interfering substances, the unbound unkown or the unbound labeled component.

The drawing as a further illustration shows an exploded perspective view of one form of the disclosed device. The drawing shows a cylindrical tubular body 11 having a fixed geometry and terminating at one end in a tapered tip portion 13. The body 11 is formed of polypropylene or other suitable material and is selectively sealable at the tapered tip portion 13 by means of friction fit cap 12, which fits over and is adapted to removably close the tip portion 13. A quantity of a matrix 15 having specific binding partners immobilized therewith is supported within the body 11 by means of a porous polyethylene disc 14 in the lower portion of the body 11. A preservative mixture 16, for use in transportation and storage such as saline solution with a bacteriocide added, or a portion of either fluid phase during operation of the device, may be retained in the upper portion of the body 11 as shown. The upper end of the body 11 may be formed with an outwardly projecting flange 17 for use in holding the body 11 in an upright position in a suitable rack. Removable cap 18 is provided for sealing the upper end of the body 11 during transportation and storage.

The eluting liquid used in step (b) must be capable of eluting the column of substantially all of the remaining unbound labeled component originating from the reference sample. Generally, this eluting liquid merely separates the liquid on the column from the column physically. This eluting liquid is preferably a buffer having the capacity to maintain a pH range appropriate to the specific binding reaction involved. The optimum pH range is generally determined with the intention of maximizing the binding affinity between the specific binding substance and its binding partner and minimizing the affinity of interfering substances for the material comprising the matrix. Both inorganic and organic buffers may be used, the choice of a particular buffer depending on the specific binding reaction involved. It may also be desirable to include a detergent in the eluting liquid to aid in the elution of interfering substances from the fluid sample.

While it has been found to be unnecessary, the disclosed saturation assay method may comprise the additional step of contacting the column with the eluting liquid capable of eluting from the column substantially all of the remaining unbound unknown from the fluid sample between steps (a) (1) and (a) (2). This eluting liquid may be chosen according to the same parameters described in the paragraph next above and, if used, is generally the same liquid as that used in step (b). This step has been found to be generally unnecessary since the reference sample itself acts as an eluting liquid by physically removing from the column substantially all of the remaining unbound unknown originating from the fluid sample.

The column is preferably equilibrated prior to step (a) by contacting the matrix with an equilibrating liquid. This liquid is preferably a buffer and establishes the optimum conditions for the specific binding reaction. It is generally the same liquid as that used in step (b).

Contact between the solid phase and the fluid phase is accomplished by passing the fluid phases through the disclosed device. The passage of both fluid phases, namely the fluid sample containing the unknown and the reference sample, involves introducing the fluid phases to the device at an open end of the body, resulting in contact with the solid phase. The time of contact between the said phase and a fluid phase is determined by the magnitude of the force exerted on the fluid phase and the flow characteristics of the solid phase. The force exerted on the fluid phases in order to effect passage through the device may include the use of such means as mechanical and pneumatic pumps, vacuum suction, and so forth. A preferable means of effecting passage of the sample is through the operation of gravity.

It is preferred that the flow characteristics of the solid phase be such that the solid phase exhibit a sponge-like fluid retention property under the influence of gravity. A matrix density can be selected which will result in such properties. Fluid retained in the matrix may then be displaced by adding additional fluid to the device. Thus, once a fluid phase is added to the solid phase and retained thereby, the phases are effectively in a state of incubation until another fluid, such as a buffer, is added to displace the retained fluid.

Where the solid phase is such that it does not possess this sponge-like retention property, where forces greater than gravity are exerted on the fluid phase, or where sample sizes are large, the outlet end of the body is preferably made selectively sealable such as through the use of a valve means or cap. The selectively sealable open end of the body may be manipulated so as to be open, partially sealed, or wholly sealed. The partially sealed state may be chosen in order to decrease the flow rate and provide an increased time of contact between the solid phase and the liquid phases, while the wholly sealed position may be chosen in order to place the solid phase and fluid phase in a state of incubation.

The length of incubation in all cases may vary between a few minutes to a few days with a preferred range of about from 15 minutes to overnight, or 12 hours. Such an incubation period is desirable in order to insure as near a quantitative reaction of the unknown and the labeled component as possible in the sequential flow of the fluid phases through the device.

The choices of a particular matrix material, a particular means for immobilizing the binding partners, a particular matrix density, a particular geometry of the body of the device, a particular means of effecting flow of the fluid phases through the device, and whether the passage of the fluid phases be prolonged for predetermined incubation periods which incubation periods may be the same or different, are all to be made in view of attaining a valid quantitative saturation technique. In order to attain adequate quantitative results using either an equilibrium, a direct or a saturation technique, the amount of specific binding sites in the solid phase, the respective sizes of the fluid phases, and their respective times of contact with the solid phase should be held constant with respect to the method used in obtaining standard values. Standard values are obtained by assaying various fluids containing known standard amounts or concentrations of the component to be determined. Thus, the percent retention of the labeled component in testing unknown samples can be directly compared to the standard values if the same procedures are followed using a predetermined amount of the unknown sample in place of the standard fluid.

The, the extent of binding of the labeled component is dependent upon the matrix parameters, namely, the amount of the binding partners immobilized with the matrix, the extent of the inhibition due to the means of immobilization, and the size of the fluid sample, as well as upon the concentration of the unknown in the sample. With the exception of the concentration of the unknown, the other factors stated above may be controlled and adjusted to give measurement ranges which are reliable over the expected range of concentration of the unknown. Usually, the parameters for the matrix are adjusted to a point where between 30 and 50 percent of the amount of the labeled component from the reference sample will become bound and be retained in the column following a particular procedure where the fluid sample does not contain any of the component to be determined. The same procedure is then used in the later testing of unknowns.

Any substance which exhibits specific binding affinity may be quantitatively determined by the method and device of the present invention. The utilization of the their binding partners in the present invention provides means of specifically detecting any substance capable of reacting with a specific binding partner based on their mutual specific binding affinity. Such substances include, in particular, insulin, proinsulin, growth hormone, angiotensin I and II, human placental lactogen, human chorionic gonadotropin, luteinizing hormone, thyroid stimulating hormone, parathormone, progesterone, aldosterone, cholesterol, follicle stimulating hormone, testosterone, vitamin D group, erythropoietin, alpha-1-anti-trypsin, renin, and morphine. Other substances which may be determined include corticoids, lysotropin, vasopressin, oxytocin, relaxin, gastrin, bradykinin, calcitonin, plasmin, glucagon, vitamin B group, bulbogastrone, estrogens, digoxin, digitoxin, Australian antigen, tetanus toxin, and so forth.

The labeled component contained in the reference sample may be labeled by such means as radioactive labels, enzyme-substrate labels, and so forth. In the enzyme-substrate labeled system, the substance to be labeled is chemically bound or coupled to either an enzyme or its substrate using conventional techniques which avoid substantial inhibition of the enzymatic active site. Some substances may be directly reacted with either an enzyme or its substrate to form the labeled component whereas others require the use of chemical coupling agents such as carbodiimides, diisocyanates, glutaric aldehyde, bis-diazobenzidine, and the like. The amount of the labeled component retained in the column may be determined by performing an enzymatic assay on the eluate or on the column itself. The enzymatic assay may employ either colorimetric, spectrophotometric, or fluorimetric techniques. Radioactive labeling may be accomplished by any standard technique without limiting the present invention.

Labeling isotopes useful in radioactive labeling include $^{125}I$ (iodine 125), $^{131}I$ (iodine 131), $^{14}C$ (carbon 1 14), $^{3}H$ (tritium), and so forth. $^{125}I$ is preferably used since iodination is a generally available labeling technique and since $^{131}I$ has a relatively shorter half life. Radioactive labeling may be accomplished by direct labeling of the substance to be labeled or by labeling a second substance which forms a conjugate with the substance to be labeled without substantially inhibiting its specific binding capacity. If the column has a fixed geometry, the amount of the labeled component retained in the column can be determined by measuring the amount of radioactivity emanating from the column and comparing the measurement to standards. Alternatively, the radioactivity of the eluate can be measured and compared to standard values. The reference sample comprises the labeled component in a fluid, such as a buffer, which is inert with respect to the unknown bound to the solid phase.

Fluid samples which may be assayed using the method herein described include inorganic and organic solutions of specific binding substances. The size of the fluid sample is theoretically infinite since the disclosed device is a flow-through system. For a particular method and device, more dilute samples containing specific binding substances may be determined by passing larger sample volumes through the device, since it acts as a concentrating as well as a separating device. Since the reaction rate between the specific binding substance and its binding partner in the solid phase-fluid phase interaction is concentration dependent, an increased effective concentration can be achieved, thus reducing incubation times. The present invention provides a particularly useful method and device in the determination of specific binding substances in body fluids and tissue extracts. Such body fluids include amniotic, cerebral and spinal fluids, serum, plasma, and urine.

The present invention comprises many advantages over prior art specific binding assays and devices as well as those advantages inherent in specific binding assays over alternative methods and devices. Inherent advantages in such a specific binding assay are specificity, sensitivity, precision, and reliability. The use of a two-phase flow-through system provides a method and device having the following advantages with respect to the prior art: the present invention enables assays to proceed in less time, usually within one hour, and readily adapts to dilute unknown samples, since the disclosed device acts as a concentrating device; it enables ready separation of the bound labeled component from that which is unbound without excessive manipulation, since the disclosed device acts as a separating device; it enables ready separation of extraneous interfering substances in the fluid sample, since the disclosed device acts as a purifying device; it provides a means for manipulating the unknown and the labeled component in the same media; and it provides a means for conducting the assay and counting the resulting radioactivity in the same system where the label is a radioactive label. Using the method and device of the present invention suitable dose response curves are generally obtained with incubations of less than 30 minutes. Separation of the bound labeled component from that which is unbound is able to be accomplished without excessive manipulation of the test system. The system is capable of performing the multiple functions of purification, separation, and concentration of the sample tested. Centrifuging and filtering steps are not required, since the unbound labeled component may be readily washed from the flow-through system.

The present invention will now be illustrated, but should not be construed as limited, by the following examples.

EXAMPLE 1

This Example relates to the use of the present method and device in obtaining a dose response curve for the determination of insulin, including the preferred equilibration and incubation steps, whole, unfractionated antiserum being used in the Sepharose coupling step.

a. Production of insulin antibodies

Capybaras were injected with priming inocula consisting of a homogenized 50/50 mixture of 8 mg/ml zinc crystalline procine insulin (dissolved in 0.01N HC1 and neutralized with 0.01N NaOH) and Freund's complete adjuvant. Each footpad was injected with 0.25 ml of the homogenate. On days 21, 23, 56 and 58, 0.25 ml of booster inocula was injected at subcutaneous sites at the four quarters of the animals. The booster inocula consisted of 8 mg/ml zinc crystalline porcine insulin mixed with an equal volume of Freund's incomplete adjuvant. On day 68, the animals were test bled and a final booster administered when the titer approached zero (approximately 70 days later). Ten days after the final booster the animals were exsanguinated.

b. Preparation of the test device

CNBr-activated Sepharose 4B, available from Pharmacia AB, Uppsala, Sweden, was swollen in 0.001M HC1 for 15 minutes and washed on a glass scintered funnel with 0.001M HC1. The whole, unfractionated antiserum was then coupled to the CNBr-activated Sepharose 4B by mixing the whole, unfractionated antiserum from procedure a. with a volume of 0.2M citrate buffer (pH 6.5) equal to that of the packed Sepharose and then adding this mixture to the swollen Sepharose. The resulting mixture was stirred overnight at 4° C. The antibody-coupled Sepharose suspension was washed with 0.2M citrate buffer (pH 6.5) until the optical density of the washings at 280 nm was less than 0.05 and then was washed with 0.9% saline solution until the optical density of the washings at 215 nm was less than 0.05. The antibody-coupled Sepharose was diluted with plain uncoupled Sepharose to a point where 30–50% of the amount of the radioactive labeled insulin was retained in the column following procedure c. below, where the fluid sample tested contained no insulin. It was then slurried with 0.9% saline solution containing 0.1% $NaN_3$ and added to 3 ml plastic Stylex syringes, available from Pharmaseal Laboratories, Glendale, California, fitted with polyethylene support disks (similar in shape and structure to the column depicted in the drawing) to give 1 ml packed Sepharose columns.

c. Performance of the assay

The packed columns were equilibrated by adding 20 ml portions of a borate buffer (pH 9.0) to the columns and allowing them to drain. The borate buffer was prepared by mixing 50 ml 0.1M $KCl/H_3BO_3$, 20.8 ml 0.1M NaOH, 1.7 ml 30% human serum albumin, and 27.5 ml $H_2O$. Porcine insulin standards were prepared for the following insulin concentrations: 50μ units/ml, 100μ units/ml, and 250μ units/ml. A control containing no insulin and the three insulin standards were added to columns prepared according to procedure b. above in 0.5 ml volumes and allowed to incubate for 25 minutes. The reference sample containing insulin labeled with $^{125}I$ was then added to each column in 0.5 ml portions and allowed to incubate for 25 minutes. During this time the columns were counted using a Gammacord gamma counter (available from Miles Laboratories, Inc. Elkhart, Indiana. The columns were washed with 10 ml of the borate buffer and counted again. The results were as follows (with % bound being calculated based on setting 100% bound as the % bound of the control):

| Insulin Concentration μ units/ml | % Bound |
|---|---|
| 0 | 100 |
| 25 | 66 |
| 50 | 43 |
| 100 | 28 |
| 250 | 17 |

These data could then be plotted graphically to form a standard curve and unknown samples could be assayed by comparing the percent labeled insulin bound to this standard curve.

EXAMPLE 2

This Example relates to the use of the present method and device in obtaining a dose response curve for the determination of human placental lactogen (HPL).

a. Production of HPL antibodies

Rabbits were injected with priming inocula consisting of a 50/50 mixture of 2.8 mg/ml HPL antigen in physiological saline solution (0.9%) and Freund's complete adjuvant. Each footpad was injected with 0.2 ml of this mixture. On days 21, 23, 56, 58, 91, 93, 126 and 128, 0.5 ml of booster inocula per day was injected intravenously into the animals. The booster inocula consisted of 0.7 mg/ml HPL antigen in physiological saline solution. Test bleedings were made on days 36 and 70, and on day 140 the animals were exsanguinated b. Preparation of the test device

The columns were prepared as in Example 1 using whole unfractionated HPL antiserum from procedure a. above.

c. Performance of the assay

The procedure as in Example 1c. was followed except that the borate-human serum albumin buffer was prepared to pH 8.0, the incubation times were 30 minutes, and the reference sample contained HPL labeled with $^{125}I$. The HPL standard solutions were prepared to concentrations of 0.32 ng/ml, 1.6 ng/ml, 8 ng/ml, 40 ng/ml, 200 ng/ml and 1000 ng/ml. The results were as follows (with % bound being calculated based on setting 100% bound as the % bound of the control):

| HPL Concentration ng/ml | % Bound |
|---|---|
| 0 | 100 |
| 1 | 98 |
| 15 | 70 |
| 62 | 42 |
| 1000 | 9 |

Using this assay, normal serum was found to contain negligible amounts of HPL while term pregnancy sera contained between 2000 and 12,000 ng/ml of HPL.

EXAMPLE 3

This Example relates to the use of the present method and device in obtaining a dose response curve for the determination of digoxin.

a. Preparation of digoxin-BSA conjugate 400 mg of digoxin was suspended in 20 ml of absolute ethanol at ambient temperature. 0.45 g of sodium metaperiodate in 20 ml of water was added dropwise with stirring. After 25 minutes, 0.5 ml of 1M ethylene glycol was added. Five minutes later, this reaction mixture was added dropwise with stirring to 560 mg of bovine serum albumin in 20 ml of water previously adjusted to pH 9.5 with 5% $K_2CO_3$. The pH was maintained between 9.0 and 9.5 by the dropwise addition of 5% $K_2CO_3$. After 45 minutes 0.3 g of sodium borohydride in 20 ml of water was added. Three hours later, the pH was lowered to 6.5 with 1M formic acid. After 1 hour, the pH was raised to 8.5 with 1M $NH_4OH$. The entire reaction mixture was then dialyzed against distilled water overnight at 4° C. The next day, the pH was lowered to 4.5 with 0.1N HCl. After 1 hour at ambient temperature and 3 hours at 4° C., the suspension was centrifuged for 1 hour at 1500 rpm. The precipitate was dissolved in 21 mil of 0.15M $NaHCo_3$, dialyzed against distilled water for 4 days, and lyophilized.

b. Production of digoxin antibodies

Rabbits were injected with inocula consisting of a 50/50 mixture of 4 mg/ml digoxin-bovine serum albumin conjugate, prepared according to the method described in procedure a., in 0.0075M phosphate-0.15M NaCl buffer (pH 7.0) and Freund's complete adjuvant. Four sites along the neck and back of the animals and each footpad were injected with 0.1 ml of this mixture. This procedure was repeated on the first and third weeks. Also, every second week the rabbits were injected intramuscularly with 0.4 ml of the inoculum. At one month intervals, ear bleedings were taken.

c. Preparation of the test device

One (1.0) gram of CMBr-activated Sepharose 4B available from Pharmacia AB, Uppsala, Sweden, was added to 200 ml of 0.001N HCl, mixed for 15 minutes, and filtered under vacuum. The swollen Sepharose 4B was then washed with 200 ml of PBS buffer (0.0075 M phosphate-0.15M NaCl, pH 7.0) and resuspended in 3.0 ml of PBS buffer. Whole, unfractionated, diluted antiserum from procedure b. was added with stirring. The reaction mixture was stirred for 2 hours at ambient temperature and then for 22 hours at 4° C. The antibody-coupled Sepharose 4B suspension was washed with 400 ml of PBS buffer and an equal volume of PBS buffer containing 0.1% $NaN_3$ was added. This mixture was in turn diluted with the addition of a 50% suspension of Sepharose 4B in distilled water to give a final dilution of antibody-coupled Sepharose 4B which would bind about half of the radioactive labeled antigen following procedure d. below where the fluid sample tested contained no digoxin. Two (2.0) ml volumes of the diluted antibody-coupled Sepharose 4B were added to 3 ml plastic Stylex syringes, available from Pharmaseal Laboratories, Glendale, California, fitted with polyethylene support disks to give 1 ml Sepharose 4B columns.

d. Performance of the assay

The columns were then equilibrated with 10 ml volumes of PBS buffer and allowed to drain. Standard diogoxin solutions were prepared for the following digoxin concentrations: 0.5 ng/ml, 1.0 ng/ml, 2.0 ng/ml, 3.0 ng/ml, 4.0 ng/ml, and 5.0 ng/ml. A control containing no digoxin and the six digoxin standards were added to columns prepared according to procedure c. above in 0.5 ml volumes and allowed to incubate for 30 minutes. The reference sample containing 3-0-succinyl digoxigenin tyrosine $^{125}I$ solution was then added to each column in 0.5 ml portions and allowed to incubate for 30 minutes. The columns were then counted using a Gammacord gamma counter. The columns were washed three times with 3.0 ml volumes of PBS buffer and counted again. The results were as follows (with % bound being calculated based on setting 100% as the % bound of the control):

| Digoxin Concentration ng/ml | % Bound |
| --- | --- |
| 0.0 | 100 |
| 0.5 | 92 |
| 1.0 | 79.5 |
| 2.0 | 60.2 |
| 3.0 | 49.0 |
| 4.0 | 41.3 |
| 5.0 | 34.7 |

Unknown samples could be assayed using the standard curve plotted from these data, as described in Example 1c.

EXAMPLE 4

This Example relates to the use of the present method and device in obtaining a dose response curve for the determination of digitoxin.

a. Preparation of digitoxin-BSA Conjugate 90 mg of digitoxin was suspended in 4 ml of ethanol at ambient temperature. 4 ml of a 0.1M sodium metaperiodate solution was added dropwise. The resulting solution was stirred for 25 minutes and 4 drops of 0.1M ethylene glycol was added. This solution was slowly added to 130 mg of bovine serum albumin in 4 ml of water previously adjusted to pH 9.5 with 5% $K_2CO_3$. The pH was maintained between 9.0 and 9.5 with 5% $K_2CO_3$. After 45 minutes, 0.05 g of $NaBH_4$ ml of water was added. After 3 hours the pH was lowered to 6.5 with 1M formic acid. After 1 hour, the pH was raised to pH 8.5 with 1M $NH_4OH$ and the mixture was dialyzed against distilled water overnight at 4° C. The next day, the suspension was centrifuged for 2 hours at 1500 rpm. The supernatant was concentrated to 6 ml in an Amicon U-2 ultrafilter, available from Amicon Corporation, Lexington, Massachusetts, and lyophilized.

b. Production of digitoxin antibodies

The same procedure as described in Example 3 was followed except that the digitoxin-bovine serum albumin conjugate was prepared according to the method described in procedure a. above and this conjugate was dissolved in a few drops of dilute NaOH before being mixed with the PBS buffer.

c. Preparation of the test device

The same procedure as described in Example 3 was followed.

d. Performance of the assay

The same procedure as described in Example 3 was followed except that the columns were equilibrated with 10 ml of PBS buffer containing 0.1% Tween 20, a detergent available from the Atlas Powder Company, Wilmington, Delaware, and that PBS buffer containing 0.1% Tween 20 was used in place of PBS buffer. The standard digitoxin solutions were prepared to the following concentrations: 5 ng/ml, 10 ng/ml, 20 ng/ml, 30 ng/ml, 40 ng/ml, and 50 ng/ml.

The results were as follows (with % bound being calculated based on setting 100% bound as the % bound of the control):

| Digitoxin Concentration ng/ml | % Bound |
| --- | --- |
| 0.0 | 100 |
| 5.0 | 83 |
| 10.0 | 73.5 |
| 20.0 | 64 |
| 30.0 | 56.6 |
| 40.0 | 50.2 |
| 50.0 | 42 |

Unknown samples could be assayed using the standard curve plotted from these data, as described in Example 1c.

EXAMPLE 5

This Example relates to the use of the present method and device in obtaining dose response curves for the determination of Vitamin $B_{12}$ wherein an equilibrium method is followed.

a. Preparation of the test device

Intrinsic factor (17), a Vitamin $B_{12}$ binder available from Nutritional Biochemicals Corp., Cleveland, Ohio, was covalently coupled to CNBr-activated Sepharose 4B, available from Pharmacia AB, Uppsala, Sweden, according to the method described in *Scand. J. Clin. Lab. Invest.* 27:151 (1971). The intrinsic factor (17)-coupled Sepharose 4B was diluted with plain uncoupled Sepharose 4B to a point where 40-60% of the radioactive labeled Vitamin $B_{12}$ was retained in the column following procedure *b.* below where the fluid sample contained no Vitamin $B_{12}$. Radioactive Vitamin $B_{12}$ ($^{57}$Co cyanocobalanin), available from Amersham/Searle, Arlington Heights, Illinois, was used. The diluted mixture was slurried with 0.9% saline and added to 3 ml plastic syringes to give 1 ml packed Sepharose columns as in Example 1b.

b. Performance of the assay

Standard Vitamin $B_{12}$ solutions were prepared for the following concentrations: 2000 pg/ml, 1000 pg/ml, 500 pg/ml, 250 pg/ml, 125 pg/ml, 63 pg/ml and 31 pg/ml. A control containing no Vitamin $B_{12}$ and the seven Vitamin $B_{12}$ standards were respectively mixed in 0.5 ml volumes with the radioactive labeled Vitamin $B_{12}$ solution to give final volumes of 1 ml. These mixtures were added to columns prepared as in procedure *a.* above and allowed to incubate for 90 minutes. The columns were then washed with 6 ml. volumes of assay buffer (prepared as described in *Scand. J. Clin. Lab. Invest.* 27: 151 [1971]) and counted using a Gammacord gamma counter. The results were as follows (with % bound being calculated based on setting 100% bound as the % bound of the control):

| Vitamin $B_{12}$ Concentration pg/ml | % Bound |
| --- | --- |
| 0 | 100.0 |
| 31 | 94.9 |
| 63 | 87.8 |
| 125 | 79.8 |
| 250 | 65.6 |
| 500 | 44.7 |
| 1000 | 24.2 |
| 2000 | 13.6 |

Unknown samples could be assayed using the standard curve plotted from these data, as described in Example 1c.

EXAMPLE 6

This Example relates to the use of the present method and device in obtaining dose response curves for the determination of human placental lactogen (HPL) wherein the labeled HPL is in an enzyme labeled form.

a. Preparation of enzyme labeled HPL

HPL was labeled with peroxidase according to the method described in *Immunochemistry* 6: 43(1969) with the following modifications: 10 mg (HPL and 10 mg horseradish peroxidase were dissolved in 1.4 ml of 0.05M carbonate buffer (pH 9), 0.05 ml of 3% glutaraldehyde solution was added to the mixture. The mixture was then rotated at ambient temperature for 90 minutes and then dialyzed against 128 ml of 0.1M borate buffer (pH 8) with several buffer changes.

b. Preparation of the test device

The same procedure as in Example 1b was followed.

c. Performance of the assay

The packed columns were equilibrated by adding 20 ml portions of a borate buffer (pH 9) to the columns and allowing them to drain. The borate buffer was prepared as in Example 1c. HPL standards were prepared for the following HPL concentrations 1000 ng/ml and 62 ng/ml. A control containing no HPL and the two HPL standards were added to columns, prepared according to procedure *b* above in 0.5 ml volumes and allowed to incubate for 25 minutes. The reference sample containing peroxidase labeled HPL, prepared as in procedure *a.* above, was then added to each column in 0.5 ml portions and allowed to incubate for 25 minutes. The columns were washed with 10 ml volumes of 0.1M borate buffer (pH 8) followed by 3 ml volumes of 0.1M phosphate buffer (pH 6). A substrate-indicator solution, prepared by mixing 0.28 ml of 0.03% $H_2O_2$ in water, 0.1 ml of 0.25% 3,3'-dimethylbenzidine, and 0.12 ml of 0.1M phosphate buffer (pH 6), was added to each column and allowed to incubate for 10 minutes. The columns were each washed with a 3 ml of volume of 0.1N HCl and the optical density (OD) of the washings were read at 460 nm with the following results:

| HPL Concentration ng/ml | $OD_{460}$ | % Color Bound |
| --- | --- | --- |
| 0 | 1.2 | 100 |
| 62 | 0.96 | 63 |

-continued

| HPL Concentration ng/ml | OD$_{460}$ | % Color Bound |
|---|---|---|
| 1000 | 0.78 | 35 |

Unknown samples could be assayed using the standard curve plotted from these data, as described in Example 1c.

EXAMPLE 7

This Example relates to the use of the present method and device in the determination of hepatitis B antigen wherein a direct radioimmunoassay technique is followed.

a. Production of hepatitis B antibodies

Anteserum containing hepatitis B antibodies were obtained following the procedure described in *The Journal of Immunology*, Vol. 109, No. 4 at Page 835.

b. Preparation of the test device

CNBr-activated Sepharose 4B, available from Pharmacia AB, Uppsala, Sweden, was swollen in 0.001M HCl. The antibodies contained in the antiserum prepared according to procedure a. above were coupled to the swollen CNBr-activated Sepharose 4B by mixing the antiserum with the Sepharose gel slurry in the proportions of 5-20 mg protein per gram of activated Sepharose 4B for 1 hour at 25° C. The resulting mixture was stirred for 17 hours at 4° C. The antibody-coupled Sepharose suspension was alternately washed with a buffer containing 0.1M tris (hydroxymethyl) aminomethane-0.5M NaCl adjusted to pH 8.2 with HCl and a buffer containing 0.1M sodium acetate-0.5 NaCl adjusted to pH 4.0 with acetic acid. The washed antibody-coupled Sepharose was slurried in tris (hydroxymethyl) aminomethane to give a 50% Sepharose suspension and 1-2 ml of this slurry was added to 3 ml plastic Stylex syringes, available from Pharmaseal Laboratories, Glendale, California, fitted with polyethylene support disks.

c. Performance of the assay

Sera which was either positive or negative with respect to the presence of hepatitis B antigen were added to the columns prepared according to procedure b. above in 0.1 ml volumes and allowed to incubate for 30 minutes. The reference sample containing hepatitis B antibody labeled with $^{125}$I according to the precedure described in *The Journal of Immunology*, Vol. 109, No. 4 at Page 835 was then added to each column in 0.1 ml portions and allowed to incubate for 1½ hours. The columns were washed with 25 ml of buffer containing 0.1M tris (hydroxymethyl) aminomethane $-0.5$ NaCl-0.01% Tween 20 (a non-ionic surfactant available from the Atlas Powder Co., Wilmington, Delaware), and then counted using a Gammacord gamma counter. It was found that about 12 times more labeled antibody was retained in the columns that were contacted with positive sera than those contacted with negative sera.

What is claimed is:

1. A method for the quantitative determination of a specific binding substance which method comprises the steps of:
   a. contacting a matrix contained in a column with a predetermined quantity of a liquid sample containing said substance to be determined and with a predetermined quantity of a reference sample containing a labeled form of said substance to be determined or a specific binding partner thereto, said matrix being porous and insoluble with respect to said liquid sample and said reference sample and having specific binding partners to said substance to be determined immobilized therewith;
   b. contacting said matrix with a liquid capable of eluting from said matrix substantially all of the labeling component originating from the reference sample and not bound to the specific binding partners immobilized with said matrix a predetermined period of time after step (a); and
   c. determining the relative amount of said labeled component which is retained in said column, which relative amount is a function of the amount of said substance to be determined in said liquid sample.

2. A method as in claim 1 wherein step (a) is accomplished by contacting said matrix with a mixture comprising a predetermined quantity of said liquid sample and a predetermined quantity of said reference sample, the amount of specific binding partners immobilized with the matrix being in excess of that capable of binding with the total amount of both the substance to be determined in the liquid sample and the labeled component in the reference sample in the time that the mixture and the matrix are in contact prior to step (b).

3. A method as in claim 2 wherein said contact between said matrix and said mixture is prolonged for a predetermined incubation period.

4. A method as in claim 3 wherein said incubation period ranges from 15 minutes to 12 hours.

5. A method as in claim 1 wherein said labeled form is of said substance being determined and wherein step (a) is accomplished by:
   (1) contacting said matrix with a predetermined quantity of said liquid sample so that some of the specific binding partners immobilized with the matrix remain unbound, and
   (a) (2) thereafter contacting said matrix with a predetermined quantity of said reference sample, the amount of specific binding partners immobilized with the matrix being in excess of that capable of binding with the total amount of the substance to be determined in said predetermined quantity of fluid sample contacted with said matrix in step (a) (1) in the time that the predetermined quantity of fluid sample and the matrix are in contact prior to step (a) (2), and the amount of labeled component in said predetermined quantity of reference sample contacted with said matrix in step (a) (2) being sufficient to bind a portion or all of the remaining unbound immobilized specific binding partners in the time that said predetermined quantity of reference sample and said matrix are in contact prior to step (b).

6. A method as in claim 5 wherein said contact between said matrix and said predetermined quantity of liquid sample and said contact between said matrix and said predetermined quantity of reference sample are prolonged for predetermined incubation periods which may be the same or different.

7. A method as in claim 6 wherein said predetermined incubation periods range between 15 minutes and 12 hours.

8. A method as in claim 5 which comprises the additional step between steps (a)(1) and (a)(2) of contacting said matrix with an eluting liquid capable of eluting from the column substantially all of said substance being determined which has not become bound.

9. A method as in claim 1 wherein said labeled form is of said substance being determined and wherein step (a) is accomplished by:
   (a)(1) contacting said matrix with a predetermined quantity of said reference sample, and
   (a)(2) thereafter contacting said matrix with a predetermined quantity of said liquid sample, the amount of said labeled component in said predetermined quantity of reference sample contacted with said matrix in step (a)(1) being in excess of that capable of binding with the specific binding partners immobilized with the matrix in the time that the predetermined quantity of reference sample and the matrix are in contact prior to step (a)(2), and the amount of said substance being determined in said predetermined quantity of liquid sample contacted with said matrix in step (a)(2) being sufficient to displace a portion of the labeled component bound to the specific binding partners immobilized with said matrix in the time that said predetermined quantity of liquid sample and said matrix are in contact prior to step (b).

10. A method as in claim 9 wherein said contact between said matrix and said predetermined quantity of liquid sample and said contact between said matrix and said predetermined quantity of reference sample are prolonged for predetermined incubation periods which may be the same or different.

11. A method as in claim 10 wherein said predetermined incubation periods range between 15 minutes and 12 hours.

12. A method as in claim 1 wherein said labeled form is of a specific binding partner to said substance being determined and wherein step (a) is accomplished by:
   (a)(1) contacting said matrix with a predetermined quantity of said liquid sample, and
   (a)(2) thereafter contacting said matrix with a predetermined quantity of said reference sample, the amount of specific binding partners immobilized with the matrix being in excess of that capable of binding with the total amount of the substance to be determined in said predetermined quantity to liquid sample contacted with said matrix in step (a)(1) in the time that the predetermined quantity of liquid sample and the matrix are in contact prior to step (a)(2), and the amount of said labeled component in said predetermined quantity of reference sample contacted with said matrix in step (a)(2) being sufficient to bind a portion or all of said substance being determined bound to said immobilized specific binding partners in the time that said predetermined quantity of reference sample and said matrix are in contact prior to step (b).

13. A method as in claim 1 which comprises the additional step of contacting said matrix with a liquid capable of equilibrating the pH of the matrix prior to step (a).

14. A method as in claim 13 wherein said equilibrating liquid comprises a buffer.

15. A method as in claim 1 wherein said eluting liquid capable of eluting from the column substantially all of the remaining unbound labeled component originating from the reference sample comprises a buffer.

16. A method as in claim 1 wherein said labeled component in said reference sample is radioactively labeled.

17. A method as in claim 16 wherein said radiocative label comprises a radioactive isotope of iodine.

18. A method as in claim 16 wherein step (c) includes measuring the amount of radioactivity emanating from said column, said amount being a function of the amount of said substance being determined in said liquid sample.

19. A method as in claim 16 wherein step (c) includes measuring the amount of radioactivity in the eluate resulting from step (b), said amount being a function of the amount of said substance being determined liquid in said sample.

20. A method as in claim 1 wherein said labeled form is labeled through the coupling of one of the components comprising an enzyme labeling pair of said substance being determined wherein an enzyme labeling pair comprises an enzyme and a substrate.

21. A method as in claim 20 wherein step (c) includes performing an enzymatic assay on the column by:
   1. contacting said matrix with a fluid containing the other component comprising said enzyme labeling pair;
   2. washing said column to remove substantially all of said component which reacted enzymatically, and
   3. determining the amount of said other component which reacted enzymatically and which was washed from said column.

22. A method as in claim 20 wherein step (c) includes performing an enzymatic assay on the eluate resulting from step (b) by:
   1. contacting said eluate with other component comprising said enzyme labeling pair, and
   2. determining the amount of said other component which reacted enzymatically.

23. A method as in claim 1 wherein said substance to be determined is one of a specific binding pair of substances selected from the group consisting of antigens and their antibodies, haptens and their antibodies, enzymes and their substrates, hormones and their receptors, and vitamins and their receptors, and wherein said specific binding partner is the other comprising said specific binding pair of substances.

24. A method as in claim 23 wherein said substance being determined is selected from the group consisting of insulin, human placental lactogen, human chorionic gonadotropin, cholesterol, the vitamin B group, estrogens, digoxin, and digitoxin.

25. A method as in claim 1 wherein said matrix is made of a material comprising a polymeric substance.

26. A method as in claim 1 wherein said immobilized specific binding partner is chemically bound to said matrix.

27. A method as in claim 26 wherein said matrix is made of a material comprising a polymeric substance.

28. A method as in claim 27 wherein said polymeric substance contains a chemical group in its molecular structure selected from the group consisting of hydroxyl, primary amino and secondary amino groups.

29. A method as in claim 26 wherein said immobilized specific binding partner is chemically bound to said matrix through a coupling agent.

30. A method as in claim 29 wherein said coupling agent is selected from the group consisting of the cyanogen halides, the inorganic and organic cyanates, and the epihalohydrins.

31. A method as in claim 30 wherein said matrix comprises agarose.

32. A method as in claim 1 wherein said liquid sample is selected from the group consisting of body fluids and tissue extracts.

33. A method as in claim 1 wherein said liquid sample is serum.

* * * * *